United States Patent [19]

Shah

[11] Patent Number: 5,578,001
[45] Date of Patent: Nov. 26, 1996

[54] INFUSION APPARATUS FOR IV BAGS

[76] Inventor: Pranav N. Shah, 16 Stowe Ct., Freehold, N.J. 07728

[21] Appl. No.: 305,261

[22] Filed: Sep. 13, 1994

[51] Int. Cl.[6] .................................................. A61M 1/00
[52] U.S. Cl. .............................. 604/31; 604/51; 604/132; 604/259
[58] Field of Search .............................. 222/92, 95, 101, 222/102, 105, 181; 604/30, 31, 65, 67, 131, 132, 245, 257, 259, 262, 51

[56] References Cited

U.S. PATENT DOCUMENTS

| | | |
|---|---|---|
| 951,101 | 3/1910 | Clarke . |
| 1,352,425 | 9/1920 | Boye . |
| 1,460,204 | 6/1923 | Maraffi . |
| 1,470,534 | 10/1923 | Keiper . |
| 1,692,116 | 11/1928 | Greist . |
| 1,716,388 | 6/1929 | Sherfy . |
| 2,003,283 | 6/1935 | Chatlelain . |
| 2,110,868 | 3/1938 | Coates . |
| 2,183,060 | 12/1939 | Blake . |
| 2,206,985 | 7/1940 | Vogt . |
| 2,542,678 | 2/1951 | Keefer . |
| 2,578,472 | 12/1951 | Gunnarson . |
| 2,876,934 | 3/1959 | Brim . |
| 3,197,072 | 7/1965 | Dick ........................................ 222/102 |
| 3,198,389 | 8/1965 | Dunning ................................. 222/102 |
| 3,257,039 | 6/1966 | Trutza .................................... 222/102 |
| 3,263,862 | 8/1966 | Tazzeo . |
| 3,507,278 | 4/1970 | Wording . |
| 3,604,418 | 9/1971 | Jones . |
| 4,639,251 | 1/1987 | Kirkland . |
| 4,850,971 | 7/1989 | Colvin . |
| 5,118,011 | 6/1992 | Kopp . |

OTHER PUBLICATIONS

1994 Catalog of EMS Nursing Products, Published by: Dixie U.S.A., Inc., p. 37 "IV–Push Pressure Infuser".

*Primary Examiner*—Randall L. Green
*Assistant Examiner*—A. T. Nguyen
*Attorney, Agent, or Firm*—Weingram & Zall

[57] ABSTRACT

An infusion apparatus includes a roller assembly adapted to exert pressure on opposed sides of an IV bag to forcibly remove the fluid contents therefrom in an even and controllable manner. A sensing element mounted to the roller assembly senses the pressure exerted during the infusion operation and generates a signal to a control assembly which automatically adjusts the movement of the roller assembly in response to the pressure sensed. If the pressure sensed exceeds a predetermined level, the control assembly will activate a drive assembly to return the roller assembly to a neutral position.

25 Claims, 3 Drawing Sheets

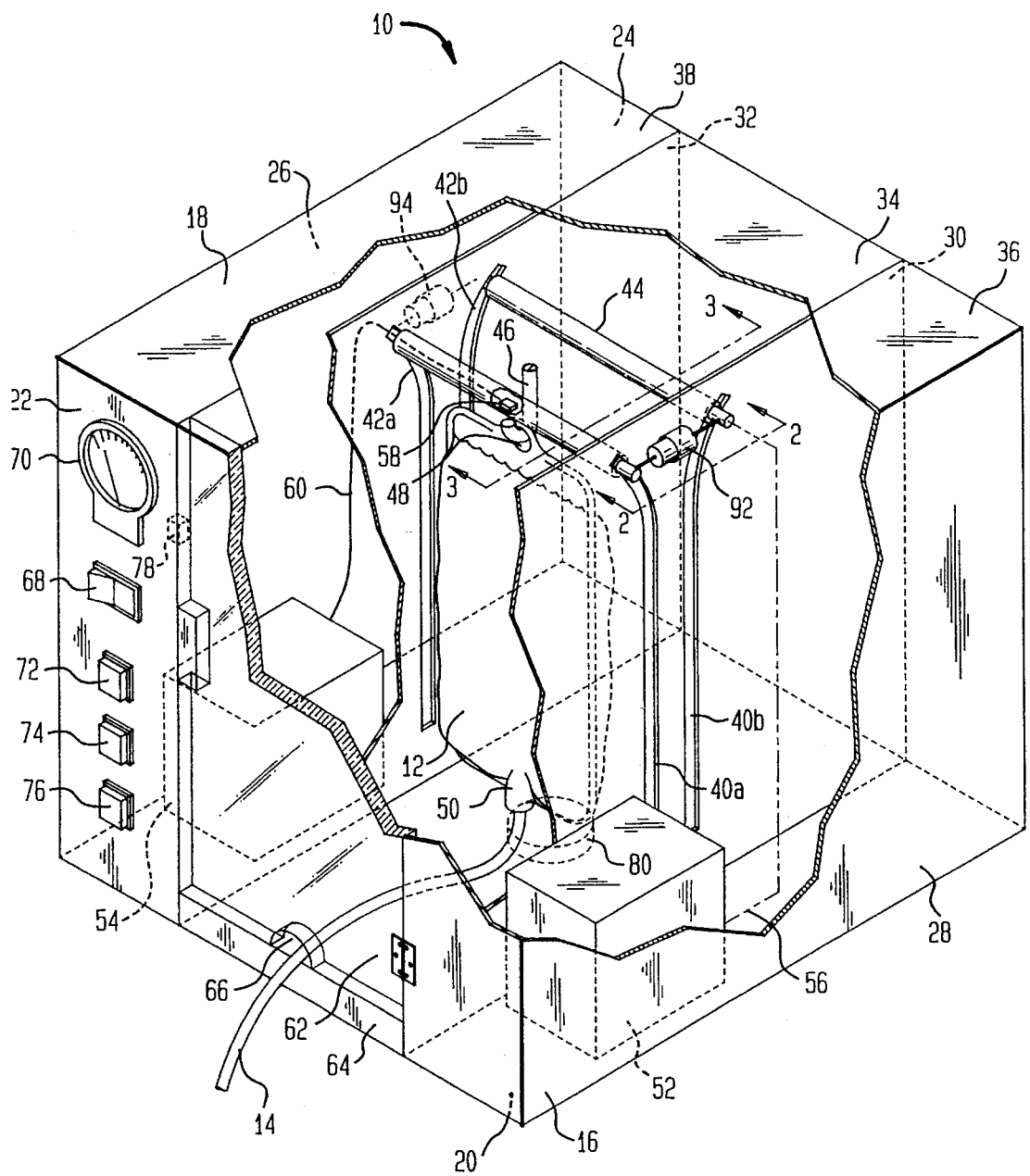

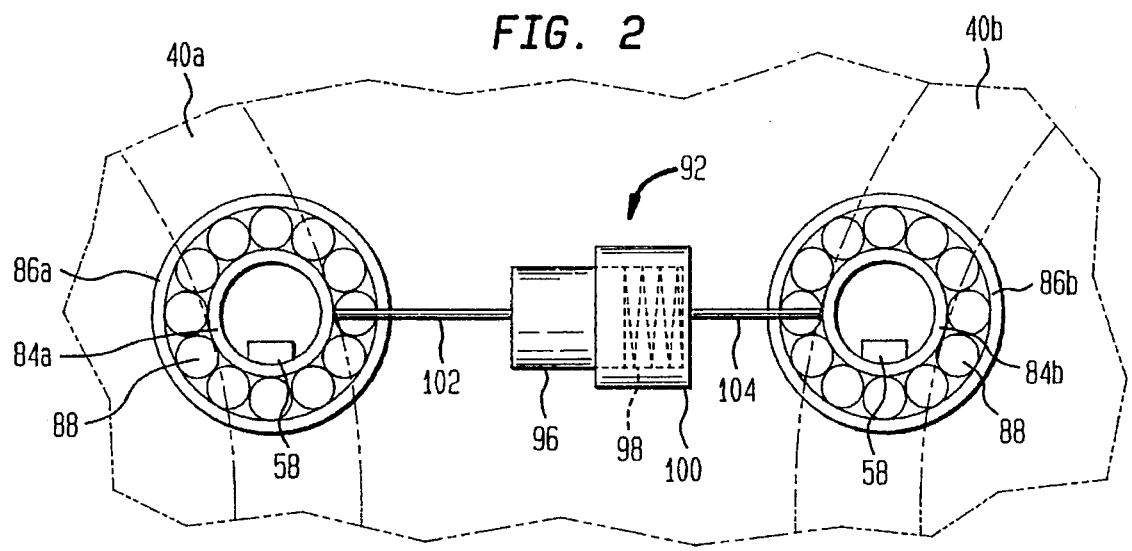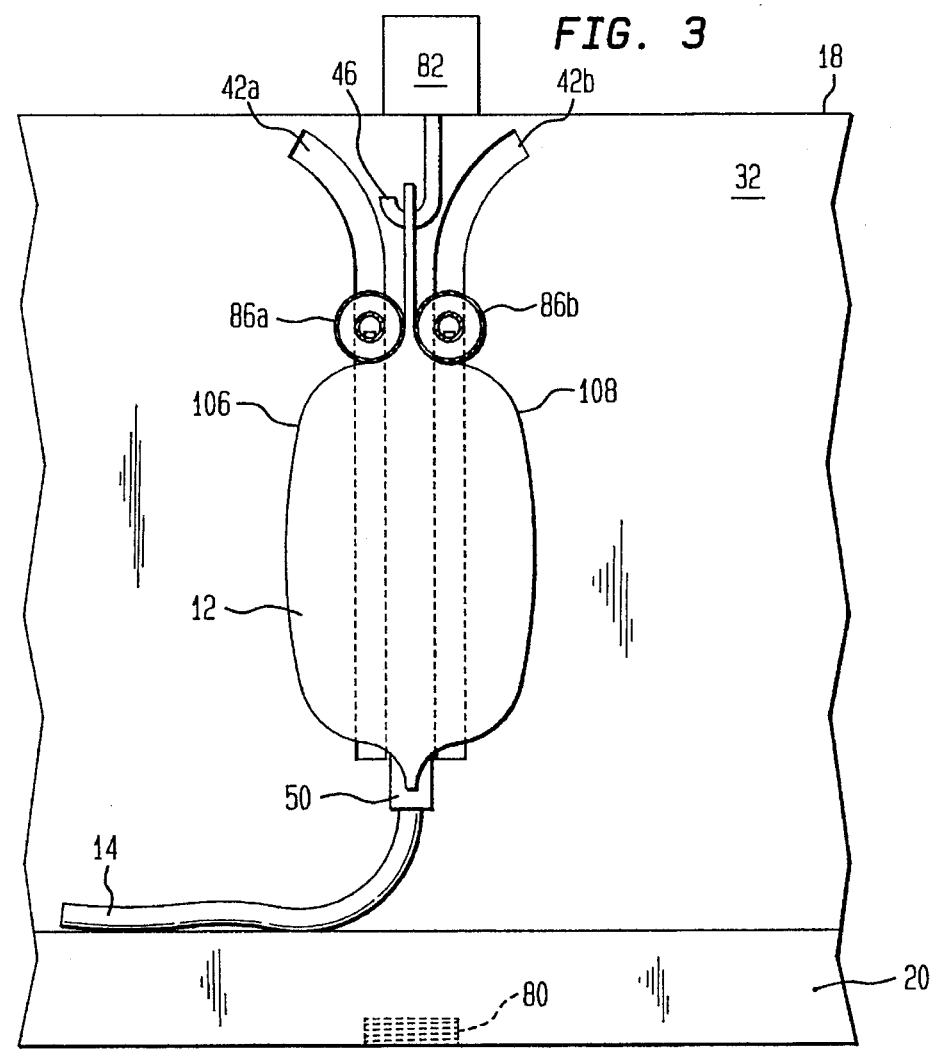

INFUSION APPARATUS FOR IV BAGS

FIELD OF THE INVENTION

This invention relates to medical devices employed to force parenteral fluid from an IV bag into a patient for an infusion operation, and particularly, to those devices that are pressure sensitive and automatically reset to receive another IV bag for a subsequent operation.

BACKGROUND OF THE INVENTION

Apparatus known for use to strip the contents of flexible, collapsible plastic containers and tubing are disclosed in U.S. Pat. Nos. 951,101 to Clarke, 1,352,425 to Bove, 1,460,204 to Maraffi, 1,470,534 to Keiper, 1,692,116 to Greist, 1,716,388 to Sherfy, 2,003,283 to Chatelain, 2,110,868 to Coates, 2,183,060 to Blake, 2,206,985 to Vogt, 2,542,678 to Keefer, 2,578,472 to Gunnarson, 2,876,934 to Brim, 3,197,072 to Dick, 3,263,862 to Tazzeo, 3,507,278 to Werding, 3,604,418 to Jones, 4,639,251 to Kirkland, 4,850,971 to Colvin and 5,118,011 to Kopp.

Among these known apparatus, the patents to Werding, Jones, Kirkland and Colvin disclose medical devices used with flexible fluid bags and tubing thereof.

In hospitals and medical facilities, it is known to use a pressure bag to strip fluid from an IV bag so that the fluid can be injected into a patient, i.e. subcutaneously, intramuscularly or intravenously. The conventional pressure bag resembles a donut shaped member with a centrally located hole into which a filled IV bag is disposed. The pressure bag is then inflated by, for example, repetitive squeezing of an air bulb, to reduce the size of the central hole and exert pressure against the IV bag. The fluid contained in the IV bag is accordingly stripped or expelled from the container through a catheter. When the IV bag has been emptied of the fluid contents, the pressure bag is deflated to remove the stripped container and to receive another filled IV bag. This process is laborious, time consuming and particularly uncomfortable for the individual inflating and deflating the pressure bag if a plurality of IV bags must be employed in, for instance, an emergency situation where a patient is to receive many units of blood, plasma, etc.

Another disadvantage is that the known pressure bag and the related medical devices must be manually reset to receive another IV bag for a subsequent stripping and infusion application.

In addition, known conventional IV pumps can strip a flexible container of parenteral fluid at a rate of approximately 1000 cc/hour, while the conventional pressure bags are more efficient and can strip the parenteral fluid at a rate of approximately 15,000 cc's/hour. In emergency situations, however, it is desirable to have an apparatus which strips the parenteral fluid from the IV bag at a still higher rate.

Moreover, the conventional pressure bag and related devices are not adapted to sense and monitor the pressure being exerted on the IV bag so that a determination can be made as to whether to increase, maintain or reduce the pressure on the IV bag. This is important because various IV fluids having different viscosities are used.

For example, among the devices used for dispensing fluids from IV bags, U.S. Pat. No. 3,507,278 to Werding discloses an apparatus for dispensing parenteral fluid, such as blood, and which includes a casing which forms a hermetic enclave into which compressed air is introduced via a valve. A flexible container with fluid is disposed within the casing and communicates with the outside of the enclave by a flexible tube. Compressed air introduced into the casing through the valve forces the fluid from the container through the tube.

U.S. Pat. No. 4,850,971 to Colvin discloses an infusion method and means which includes a tray for holding an IV bag. The tray has sides formed with longitudinal slots. A drum has cocking handles at each end which extend through a corresponding one of the slots to move from one end of the tray to the opposite end. A coil spring is mounted to the drum to pull the drum against the bag to pressure the contents therefrom.

U.S. Pat. No. 3,604,418 to Jones discloses an apparatus for stripping fluid from flexible plastic tubing, such as tubing used with blood collecting devices. The apparatus includes hinged portions, each of which is provided with a roller to be in close proximity to one another yet permit the flexible plastic tubing to pass therebetween and be stripped of any fluid remaining in the tubing. The stripped fluid is returned to the fluid dispensing bag.

None of the devices discussed above provide an infusion apparatus for an IV bag which is adapted to force parenteral fluid from the IV bag under pressure between a pair of rollers and sense the pressure to determine whether the pressure should be increased, maintained or reduced with respect to the particular infusion application. None of the devices are adapted to be automatically reset to facilitate removal of an empty IV bag and mounting of a filled IV bag for the next infusion application.

OBJECTS AND SUMMARY OF THE INVENTION

It is an object of the present invention to provide a medical apparatus and method adapted to forcibly feed parenteral fluid from an IV bag in a controlled manner for an infusion application.

It is another object of the present invention to provide an apparatus which facilitates loading of a filled IV bag and removal of the IV bag stripped of the fluid contents.

It is still another object of the present invention to provide an apparatus that uniformly forces the fluid from the IV bag so that the flow rate of the fluid can be monitored and regulated.

It is still another object of the present invention to provide an apparatus which automatically resets upon conclusion of an infusion operation to facilitate removal of the emptied IV bag and receipt of a filled IV bag for a subsequent infusion application.

It is still another object of the present invention to provide means to sense the pressure employed during the infusion operation and when the IV bag has been emptied of the parenteral fluid.

It is still a further object of the present invention to provide means for sensing, maintaining and regulating the amount of pressure being exerted on the IV bag during an infusion operation.

The foregoing objects are accomplished by providing an apparatus for feeding parenteral fluid under pressure from an IV bag to a patient, the apparatus consisting of a support member to support the IV bag, a roller assembly which includes a pair of spaced apart rollers at opposed sides of the IV bag and in parallel relationship with each other, each one of the rollers to contact a corresponding side of the IV bag to exert pressure thereon, and a drive assembly to drive the roller assembly along the IV bag.

A control assembly is also provided to interconnect the roller assembly and the drive assembly to control the drive assembly to move the roller assembly along the IV bag in response to the pressure exerted thereon.

BRIEF DESCRIPTION OF THE DRAWINGS

For a more complete understanding of the present invention, reference may be had to the following description of an exemplary embodiment of the present invention considered in connection with the accompanying drawings, in which:

FIG. 1 is a perspective view partially broken away showing a preferred embodiment of the infusion apparatus according to the present invention;

FIG. 2 is a cross-sectional view taken along lines 2—2 in FIG. 1;

FIG. 3 is a partial cross-sectional view taken along line 3—3 in FIG. 1; and

DETAILED DESCRIPTION OF THE PREFERRED EMBODIMENT

Figure 4:
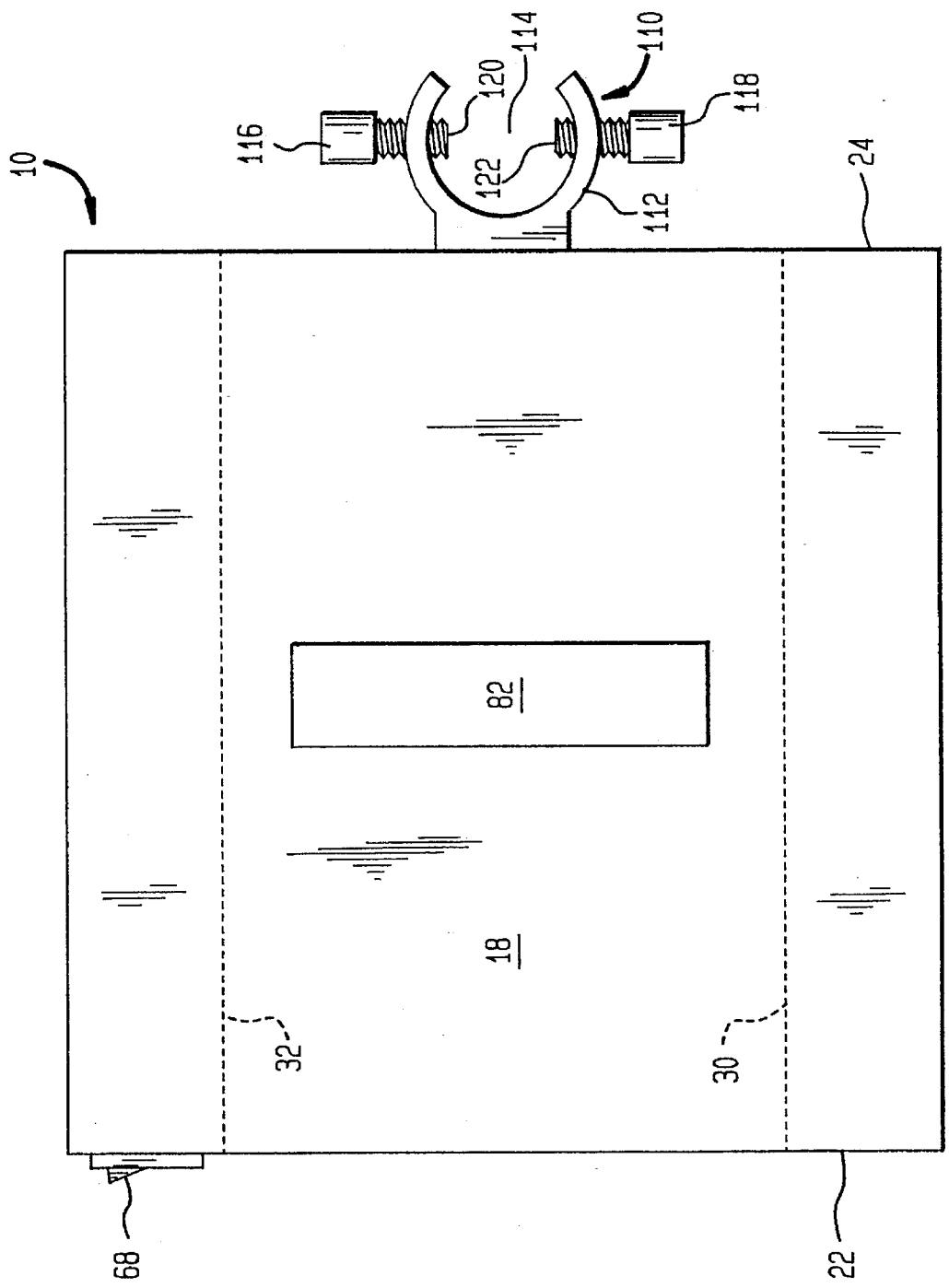
FIG. 4 is a top view of the apparatus shown in FIG. 1.

Referring to the drawings, where like reference characters indicate like parts, FIG. 1 shows a preferred embodiment of an infusion apparatus 10 according to the present invention. The infusion apparatus 10 is adapted to receive and support an IV bag 12 holding parenteral fluid. The parenteral fluid is forced from the IV bag 12 through a conduit 14 or tubing, such as a catheter, and into a patient (not shown).

As shown in FIG. 1, the infusion apparatus 10 includes a housing 16 having a top 18, a bottom 20, a front panel 22, a rear panel 24 and opposed side walls 26,28. A pair of spaced apart panels 30,32 or partitions extend from the front panel 22 to the rear panel 24, and between the top 18 and the bottom 20 of the housing 16. The panels 30,32 form a plurality of compartments 34,36,38 or chambers within the housing 16. The compartment 34 is the central compartment, while the compartments 36,38, are wing compartments which are at opposed sides of the central compartment 34.

Each one of the panels 30,32 is provided with a corresponding pair of spaced apart slots 40a,40b and 42a,42b. The pairs of slots 40a,40b and 42a,42b are similarly arranged in their corresponding panels 30,32, respectively. For example, the pair of slots 40a,40b of the panel 30 extend from a position substantially adjacent to the bottom 20 of the housing 16 to a position substantially adjacent to the top 18 of the housing 16. The slots 40a,40b are arranged substantially parallel and in close proximity to each other along the panel 30 at a distance of approximately 0.5 cm. The slots 40a,40b diverge from each other at a position near the top 18 of the housing 16. This divergence of the slots 40a,40b facilitates removing and mounting of the IV bag 12 in the central compartment 34. It is preferred that the upper ends of the slots 40a,40b diverge to be spaced from each other at a distance of approximately at least 2 cm. It is understood that these parameters are by way of example only, and that the spacing between the slots 40a,40b is selected to accommodate IV bags and their particular dimensions.

As also shown in FIG. 1, the slots 42a,42b in the panel 32 are similarly arranged having the parameters recited. The pair of slots 42a,42b are aligned with the pair of slots 40a,40b so that a slot of the pair 42a,42b in the panel 32 is in registration with a corresponding one of the slots of the other pair 40a,40b in the panel 30.

FIG. 1 shows a roller assembly 44 of the infusion apparatus 10 which is mounted in the pairs of slots 40a,40b and 42a,42b and extends from the wing compartments 36,38 across the central compartment 34.

A retaining hook 46 is secured to the top 18 of the housing 16 and extends into the central compartment 34 to a position below the roller assembly 44 when the roller assembly 44 is retracted to a position near the top 18 of the housing 16. A handle portion 48 of the IV bag 12 receives the hook 46 therethrough. The IV bag 12 accordingly hangs below the roller assembly 44 when the assembly is in the fully retracted position as shown in FIG. 1. This arrangement permits quick and efficient removal of the IV bag 12 after the fluid has been forced therefrom, and permits a full IV bag to be easily hung on the hook 46 for a subsequent infusion application without the roller assembly 44 getting in the way. The IV bag 12 is preferably held by the hook 46 off the bottom 20 of the housing 16 so that an outlet means 50 of the IV bag 12 is clear of and does not contact the bottom 20 of the housing 16.

Control assemblies 52,54 shown in FIG. 1 are disposed in a corresponding one of the wing compartments 36,38. Each one of the control assemblies 52,54 includes a drive means represented by the phantom line 56 and a sensing element 58. The control assemblies 52,54 can be used individually or in conjunction with each other. The control assembly 54 is connected to the sensing element 58 by a signal line 60. The drive means 56 is connected to the roller assembly 44. The drive means 56 can include any of the known devices to move the roller assembly from the retracted position as shown in FIG. 1, through a deployment position along the sides of the IV bag, when the roller assembly 44 proceeds along the pairs of slots 40a,40b and 42a,42b toward the bottom 20 of the housing 16.

A door 62 is hingedly connected to the front panel 22 of the housing 16 as shown in FIG. 1. A retention plate 64 is provided beneath the door 62 to retain any fluids that may accumulate in the central compartment 34. An edge of the door 62 is provided with a cutout 66 which functions as a passage through which the flexible conduit 14, such as a catheter of the IV bag, can extend when the door 62 is closed. It is preferred that the front panel 22, or at least the door 62, is formed from a transparent material so that the central compartment 34 can be seen during an infusion application.

The front panel 22 of the housing 16 is provided with controls for the control assembly 54. The controls include a power switch 68 to initiate power to the infusion apparatus. A flowmeter 70 is provided to indicate the flow rate of the fluid from the IV bag 12 as a result of the pressure being exerted on the bag 12 as the fluid contents are forced therefrom by the roller assembly 44. Switches 72,74 are used to deploy the roller assembly and reset the roller assembly, respectively. An indicator light 76 is activated by a default switch 78 in the front panel 22 of the housing 16. The light 76 indicates when the door 62 is open. The default switch 78 is provided to ensure that the roller assembly 44 will not function unless the door 62 is securely closed.

A threaded aperture 80 at the bottom 20 of the housing 16 is adapted to receive a tripod stand (not shown) used in hospitals and physicians' offices.

A handle 82 at the top 18 of the housing 16 is provided to carry the infusion apparatus 10.

Referring to FIG. 2, the roller assembly 44 of the infusion apparatus 10 is shown. The roller assembly 44 includes a pair of axles 84a,84b. Each one of the axles 84a,84b has opposed ends which are mounted to extend into a corresponding one of the slots 40a,40b and 42a,42b. The ends of the axles 84a,84b are disposed in a corresponding one of the wing compartments 36,38. The axles 84a,84b are arranged to extend across the central compartment 34 in a spaced parallel relationship with each other.

As shown in FIG. 2, rollers 86a,86b are mounted for rotation around a corresponding one of the axles 84a,84b. It is preferred that the rollers 86a,86b do not extend through the slots 40a,40b and 42a,42b and into the wing compartments 36,38. The rollers 86a,86b are preferably formed from plastic, rubber or other material that will not puncture or damage the walls of the IV bag 12 when the rollers 86a,86b are brought to bear against the exterior surface at opposed sides of the bag 12.

A plurality of ball bearings 88 are disposed between each one of the axles 84a,84b and the corresponding roller 86a,86b mounted thereto. Use of the ball bearings 88 permits the axles 84a,84b to remain stationery when being moved along the corresponding slots, while the rollers 86a,86b are free to spin about a corresponding one of the axles 84a,84b.

FIG. 2 shows the sensing element 58 which is disposed at the interior of at least one of the axles 84a,84b, preferably near the center of the axle selected. The sensing element 58 can be piezoelectric material. Although the infusion apparatus 10 will function having only one of the axles 84a,84b provided with the sensing element 58, it is understood that each one of the axles 84a,84b can be provided with a corresponding sensing element 58 disposed therein. The sensing element 58 is connected to the control assembly 54 via the signal line 60 as shown in FIG. 1.

FIG. 2 also shows the elements of the roller assembly 44. The roller assembly 44 includes a pair of spacing assemblies 92,94. The spacing assembly 92 only is shown due to the perspective of FIG. 2 (the spacing assembly 94 is shown in FIG. 1). The spacing assembly 92 interconnects the ends of the axles 84a,84b which extend into the wing compartment 36, as also shown in FIG. 1. The spacing assembly 94 is similarly arranged in the wing compartment 38 to interconnect the opposite ends of the axles 84a,84b in the wing compartment 38. By way of example and as shown in FIG. 2, the spacing assembly 92 includes a first portion 96 having essentially a cylindrical shape. A second portion 100 is also cylindrically shaped and includes a biasing member 98 such as a spring, disposed therein. The second portion 100 has a diameter greater than that of the first portion 96 so that the first portion 96 can be received in the second portion 100. The first portion 96 is biased against the spring 98 disposed in the second portion 100.

A first arm 102 connects the axle 84a to the first portion 96 of the spacing assembly 92. A second arm 104 connects the axle 84b to the second portion 100 of the spacing assembly 92. The spacing assembly 92 is therefore adapted to bias the axles 84a,84b to be maintained in the corresponding slots 40a,40b. The spacing assembly 92 ensures that the axles 84a,84b move between the retracted and extended positions along the slots 40a,40b and 42a,42b in a uniform manner. The spacing assembly 94 functions in the same way as the spacing assembly 92.

FIG. 3 shows the roller assembly 44 being deployed from the retracted position to force the fluid contents from the IV bag 12. As the roller assembly 44 is moved from the retracted position near the top 18 of the housing 16, the rollers 86a,86b are brought against corresponding opposed sidewalls 106, 108 of the IV bag 12. The rollers 86a,86b move from the fully retracted position, where the rollers 86a,86b are clear of the hook 46 so that interchanging emptied and filled IV bags is quick and easy, downward along the slots 40a,40b and 42a,42b. A portion of the IV bag 12 below the rollers 86a,86b becomes bulbous as a result of the pressure being exerted by the rollers 86a,86b to force the fluid from the IV bag 12 through the outlet means 50 to the conduit 14. The clearance between the outlet means 50 of the IV bag 12 and the bottom 20 of the housing 16 is sufficient to reduce the possibility of the bottom 20 interfering with the flow of fluid.

FIG. 4 shows a mounting assembly 110 for the infusion apparatus 10. The mounting assembly 110 is employed in those instances where the threaded tripod poles are unavailable. The mounting assembly 110 includes a collar 112 which extends from the rear panel 24 of the housing 16. The collar 112 is substantially U-shaped with a space 114 sized and shaped to receive a mounting pole or rack (not shown) typically used in hospitals and physicians' offices. Thumb screws 116,118 are threadedly engaged to opposed sides of the collar 112. Tightening of the thumb screws 114,116 moves corresponding ends 120,122 of the thumb screws into the space 114 to bear against the mounting pole and secure the infusion apparatus thereto.

The infusion apparatus 10 of the present invention is for use with IV bags holding parenteral fluids such as D-5 glucose/water solution, saline, lactated ringers, whole blood, packed cells, coagulation factors or platelets. The infusion apparatus 10 can remove the parenteral fluid from the IV bags 12 much faster and more efficiently than a standard IV pump or the conventional pressure bags. The infusion apparatus 10 is also adapted to remove the parenteral fluid from the bag in a controlled manner and to enable the user to select the flow rate, i.e. the stripping rate, with more accuracy.

During an infusion operation with the IV bag 12, the roller assembly 44 is in the retracted position near the top 18 of the housing 16. Power to the infusion apparatus 10 is initiated. The indicator light 76 will show the status of the door 62, i.e. opened or closed. The door 62 is opened to either remove an empty IV bag or to hang a filled IV bag on the hook 46 in the central compartment 46. If a new IV bag is used, the flexible conduit 14, such as a catheter, connected to the IV bag is led outward from the central compartment 34 through the cutout 66 in the door 62. The door 62 is closed overriding the default switch 78 and extinguishing the indicator light 76. The deployment switch 78 is actuated and the axles 84a,84b of the roller assembly 44 move from the retracted position downward along the slots 40a,40b and 42a,42b.

After traveling a short distance, the axles 84a,84b will begin moving toward each other as the position of the slots 40a,40b and 42a,42b converge with respect to each other. The rollers 86a,86b move closer to a corresponding one of the sidewalls 106,108 of the IV bag 12. At a point where the slots 40a,40b and 42a,42b no longer converge and are disposed in parallel relationship, each one of the rollers 86a,86b contacts and is brought to bear against a corresponding one of the sidewalls 106,108 above the fluid level in the IV bag. As the drive means 56 pulls the axles 84a,84b downward along the slots, the rollers 86a,86b exert pressure on the opposed sidewalls therebetween to force the fluid in the IV bag downward to the outlet 50. As a result of this pressure, the IV bag assumes the bulbous shape shown in FIG. 3.

The piezoelectric material 58 responds to the pressure exerted on the sidewalls 106,108 where the rollers 86a,86b are forced to overcome the pressure of the fluid remaining in the IV bag 12. The infusion apparatus is adapted to stop the movement of the rollers 86a,86b if the pressure sensed by the piezoelectric material 58 exceeds a predetermined level for a safe infusion application. This is particularly advantageous where, for example, the catheter 14 becomes clogged or pinched, or where there is an obstruction in the patient's body near the catheter, which would impede the steady flow of the fluid from the IV bag and/or possibly injure the patient or damage the infusion apparatus 10. If the pressure exerted is determined to be too high as sensed by the control assembly 52,54 and indicated by the flowmeter 70, taking into account the viscosity of the fluid in the IV bag, the roller assembly 44 rate of descent along the IV bag is reduced to alleviate the pressure, or stopped altogether.

When the fluid has been completely stripped from the IV bag and the roller assembly 44 contacts the outlet means 50, the roller assembly 44 automatically moves to the retracted position (FIG. 1). The outlet means 50 of the IV bag is generally made of a material more dense than the sidewalls 106,108 of the IV bag. This denser material is sensed by the piezoelectric material 58 which generates a signal to the control assembly 52 for the drive assembly to return the roller assembly 44 to the retracted position so that the empty IV bag can be immediately removed and replaced by another full IV bag which is easily inserted on the hook 46 for a subsequent infusion operation.

The infusion apparatus 10 of the present invention is portable and ideally suited for use in the field, as well as use in hospitals, physicians offices, etc. The apparatus 10 adjusts the flow rate of the fluid being forced from the IV bag so that an infusion operation is performed accurately despite the amount and viscosity of the fluid to be removed from the IV bag.

The infusion apparatus 10 accepts the standard IV bags, i.e. ¼, ½, ¾ or 1 liter sizes, and can be adapted to accept IV bags with larger volumes.

It will be understood that the embodiment described herein is merely exemplary and that a person skilled in the art may make many variations and modifications without departing from the spirit and scope of the invention. All such modifications and variations are intended to be included within the scope of the invention as defined in the appended claims.

What is claimed is:

1. An apparatus for feeding parenteral fluid under pressure from an IV bag to a patient, the apparatus comprising:

a support member adapted to support the IV bag;

a roller assembly comprising a pair of spaced apart rollers adapted to be placed at opposed sides of the IV bag, each one of the rollers adapted to contact a corresponding side of the IV bag to exert pressure;

a drive assembly to drive the roller assembly so that the rollers are adapted to exert pressure on the IV bag;

a control assembly interconnecting the roller assembly and the drive assembly, the control assembly constructed to control the drive assembly to move the roller assembly in response to the pressure adapted to be exerted on the IV bag; and a sensing member mounted to the roller assembly to generate a signal to the control assembly of the pressure adapted to be exerted on the IV bag.

2. The apparatus according to claim 1, further comprising:

a first biasing member, a first one of the pair of spaced apart rollers having first opposed ends, and a second one of the pair of spaced apart rollers having second opposed ends, the first biasing member connecting one of the first opposed ends of the first roller with one of the second opposed ends of the second roller.

3. The apparatus according to claim 2, further comprising a second biasing member, the second biasing member connecting another one of the first opposed ends of the first roller with another one of the second opposed ends of the second roller.

4. The apparatus according to claim 1, wherein the sensing member comprises piezoelectric material.

5. The apparatus according to claim 1, further comprising a housing with an interior compartment constructed to receive the support member, the roller assembly, the drive assembly and the control assembly.

6. The apparatus according to claim 5, wherein the housing comprises:

a door hingedly mounted to the housing to permit access to the interior compartment; and a switch responsive to movement of the door between an open and a closed position for generating a signal to the control assembly to effect movement of the drive assembly.

7. The apparatus according to claim 6, wherein at least one of the door and the housing is formed from a substantially transparent material.

8. The apparatus according to claim 6, wherein the door comprises a passage through which a flexible conduit is disposed for connection to the IV bag.

9. The apparatus according to claim 5, wherein the housing further comprises a pair of panels, the pair of panels constructed and arranged to partition the interior compartment into a pair of wing compartments and a central compartment disposed between the pair of wing compartments, the central compartment containing the support member and the roller assembly, each one of the wing compartments containing at least one of the drive assembly and the control assembly.

10. The apparatus according to claim 9, wherein the pair of panels comprises:

a first panel with a first pair of slots arranged to extend in substantially parallel relationship with each other along the first panel, and a second panel with a second pair of slots arranged to extend in substantially parallel relationship with each other along the second panel, wherein the first pair of slots and the second pair of slots are in registration with each other to receive corresponding portions of the pair of spaced apart rollers of the roller assembly.

11. The apparatus according to claim 10, wherein the first pair of slots are arranged to diverge from each other after extending in the substantially parallel relationship, and the second pair of slots are arranged to diverge from each other after extending in the substantially parallel relationship.

12. The apparatus according to claim 1, wherein the support member is a hook.

13. The apparatus according to claim 1, wherein the pair of spaced apart rollers comprises:

a first roller having first opposed end portions, and a second roller having second opposed end portions, each one of the first opposed end portions of the first roller in registration with a corresponding one of the second opposed end portions of the second roller.

14. The apparatus according to claim 13, further comprising:

a first biasing member connecting one of the first opposed end portions of the first roller with the corresponding one of the second opposed end portions of the second roller, and a second biasing member connecting another one of the first opposed end portions of the first roller with the corresponding another one of the second opposed end portions of the second roller.

15. The apparatus according to claim 13, wherein the first roller and the second roller each comprises:

an axle around which a roller is mounted, and ball bearings disposed between the axle and the roller.

16. An apparatus for feeding parenteral fluid from an IV bag to a patient, the apparatus comprising:

a housing having a top wall, a bottom wall, a front panel, a rear panel and opposed side walls surrounding an interior of the housing;

a pair of partition members disposed at the interior of the housing, the pair of partition members spaced apart to provide a central compartment, a first wing compartment and a second wing compartment, the first and second wing compartments disposed at opposite sides of the central compartment, a first one of the pair of partition members provided with a first pair of slots extending along the first partition member from a position near the top wall of the housing to a position near the bottom wall of the housing, the first pair of slots converging toward each other at a position near the top wall of the housing to assume a substantially parallel relationship, a second one of the pair of partition members provided with a second pair of slots extending along the second partition member from a position near the top wall of the housing to a position near the bottom wall of the housing, the second pair of slots converging toward each other at a position near the top wall of the housing to assume a substantially parallel relationship, slots of the first pair and the second pair of slots in registration with each other;

a support member disposed in the central compartment and adapted to support the IV bag at the central compartment;

a first roller assembly disposed in the central compartment and adapted to contact a first side of the IV bag, the first roller assembly including first opposed end portions, one of the first opposed end portions extending through a corresponding one of the first pair of slots, another of the first opposed end portions extending through a corresponding one of the second pair of slots;

a second roller assembly disposed in the central compartment and adapted to contact a second side of the IV bag opposite to the first side, the second roller assembly including second opposed end portions, one of the second opposed end portions extending through another corresponding one of the first pair of slots, another of the second opposed end portions extending through another corresponding one of the second pair of slots, wherein the first roller assembly and the second roller assembly are adapted to move between a retracted position where the first and second roller assemblies are positioned in their respective slots near the top wall of the housing above the support member with the support member disposed therebetween, and an extended position where the first and second roller assemblies have exerted pressure against the first and second corresponding sides of the IV bag to forcibly remove the fluid therefrom;

a first spacer assembly disposed in the first wing compartment of the housing to interconnect one of the first opposed end portions of the first roller assembly with one of the second opposed end portions of the second roller assembly, the first spacer assembly constructed to bias the end portions;

a drive assembly to move the first and second roller assemblies between the retracted position and the extended position; and a sensing element mounted to at least one of the first and second roller assemblies, the sensing element responsive to pressure exerted on the IV bag to generate a signal of an amount of the pressure being exerted on the IV bag.

17. The apparatus according to claim 16, further comprising:

a control assembly interconnecting at least one of the first and second roller assemblies having the sensing element with the drive assembly, the control assembly responsive to the signal generated by the sensing element to control the drive assembly to effect movement of the first and second roller assemblies.

18. The infusion apparatus according to claim 17, wherein the control assembly automatically returns the first and second roller assemblies to the retracted position after the first and second roller assemblies reach the extended position.

19. The apparatus according to claim 6, further comprising:

a second spacer assembly disposed in the second wing compartment of the housing to interconnect another of the first opposed end portions of the first roller assembly with another of the second opposed end portions of the second roller assembly, the second spacer assembly constructed to bias the other end portions.

20. The apparatus according to claim 16, wherein each one of the first roller assembly and the second roller assembly comprises;

an axle;

a roller mounted around the axle for rotational movement, and a plurality of ball bearings disposed between the axle and the roller to permit the roller to rotate around the axle.

21. The infusion apparatus according to claim 16, wherein the sensing element comprises piezoelectric material.

22. A method for feeding parenteral fluid from an IV bag to a patient, the method comprising the steps of:

exerting pressure on a first side of the IV bag and a second side of the IV bag opposed to the first side;

sensing the pressure exerted on the IV bag; and adjusting the pressure exerted at the first side and the second side of the IV bag in response to the pressure sensed.

23. The method according to claim 22, further comprising the step of:

terminating the pressure exerted on the IV bag when the pressure exceeds a predetermined amount.

24. An apparatus for feeding parenteral fluid under pressure from an IV bag to a patient, the apparatus comprising:

a support member adapted to support the IV bag;

a first guide assembly comprising:

a first guide slot and a second guide slot converging from diverged positions toward each other, a second guide assembly comprising:

a third guide slot and a fourth guide slot converging from diverged positions toward each other, the first guide slot of the first guide assembly in registration with the third guide slot of the second guide assembly;

the second guide slot of the first guide assembly in registration with the fourth guide slot of the second guide assembly;

a roller assembly comprising:
- a first roller with first opposed ends, the first roller arranged with one of the first opposed ends disposed in the first guide slot and another of the first opposed ends disposed in the third guide slot, the first roller adapted to contact a first side of the IV bag, and
- a second roller with second opposed ends, the second roller arranged with one of the second opposed ends disposed in the second guide slot and another of the second opposed ends disposed in the fourth guide slot, the second roller adapted to contact a second side of the IV bag opposite to the first side;
- the first roller and the second roller adapted to move between a first position diverged from each other at opposite sides of the IV bag to a second position where the first and second rollers converge toward the IV bag for the first roller to contact the first side of the IV bag, and the second roller to contact the second side of the IV bag opposite to the first side; and a drive assembly to drive the first roller and the second roller of the roller assembly between the first and the second positions.

25. The apparatus according to claim 24, further comprising:
a sensor element mounted to the roller assembly, the sensor element generating a signal to the drive assembly to control movement of the roller assembly between the first and second positions.

* * * * *